United States Patent
Joyce et al.

(10) Patent No.: US 11,911,038 B2
(45) Date of Patent: Feb. 27, 2024

(54) CUT OPTIMIZATION FOR EXCESSIVE TISSUE CONDITIONS

(71) Applicant: Covidien LP, Mansfield, MA (US)

(72) Inventors: Steven H. Joyce, Durham, CT (US); David E. Valentine, Hamden, CT (US); Patrick Mozdzierz, Glastonbury, CT (US); Charles R. Kollar, Washington, DC (US); Haley Strassner, Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 169 days.

(21) Appl. No.: 17/120,659

(22) Filed: Dec. 14, 2020

(65) Prior Publication Data

US 2021/0212693 A1    Jul. 15, 2021

Related U.S. Application Data

(60) Provisional application No. 62/960,202, filed on Jan. 13, 2020.

(51) Int. Cl.
| | |
|---|---|
| *A61B 17/062* | (2006.01) |
| *A61B 17/072* | (2006.01) |
| *A61B 17/115* | (2006.01) |
| *A61B 17/32* | (2006.01) |

(52) U.S. Cl.
CPC .......... *A61B 17/1155* (2013.01); *A61B 17/32* (2013.01)

(58) Field of Classification Search
CPC .......... A61B 17/115; A61B 17/320016; A61B 2017/320032; A61B 2017/07285; A61B 17/1155
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Mar. 17, 2021, corresponding to counterpart European Application 21151140.7; 9 pages.

(Continued)

*Primary Examiner* — Gloria R Weeks
(74) *Attorney, Agent, or Firm* — Carter, DeLuca & Farrell LLP (57) ABSTRACT

A method of operating a surgical stapler includes advancing a knife assembly at a first velocity until a predetermined force is detected, advancing the knife assembly at a second velocity when the predetermined force is detected, the second velocity being less than the first velocity, and continuing to advance the knife assembly at the second velocity until the knife assembly travels a cutting stroke distance.

20 Claims, 3 Drawing Sheets

(56) References Cited

U.S. PATENT DOCUMENTS

| | | | |
|---|---|---|---|
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |
| 4,476,863 | A | 10/1984 | Kanshin et al. |
| 4,485,817 | A | 12/1984 | Swiggett |
| 4,488,523 | A | 12/1984 | Shichman |
| 4,505,272 | A | 3/1985 | Utyamyshev et al. |
| 4,505,414 | A | 3/1985 | Filip |
| 4,520,817 | A | 6/1985 | Green |
| 4,550,870 | A | 11/1985 | Krumme et al. |
| 4,573,468 | A | 3/1986 | Conta et al. |
| 4,576,167 | A | 3/1986 | Noiles |
| 4,592,354 | A | 6/1986 | Rothfuss |
| 4,603,693 | A | 8/1986 | Conta et al. |
| 4,606,343 | A | 8/1986 | Conta et al. |
| 4,632,290 | A | 12/1986 | Green et al. |
| 4,646,745 | A | 3/1987 | Noiles |
| 4,665,917 | A | 5/1987 | Clanton et al. |
| 4,667,673 | A | 5/1987 | Li |
| 4,671,445 | A | 6/1987 | Barker et al. |
| 4,700,703 | A | 10/1987 | Resnick et al. |
| 4,703,887 | A | 11/1987 | Clanton et al. |
| 4,708,141 | A | 11/1987 | Inoue et al. |
| 4,717,063 | A | 1/1988 | Ebihara |
| 4,752,024 | A | 6/1988 | Green et al. |
| 4,754,909 | A | 7/1988 | Barker et al. |
| 4,776,506 | A | 10/1988 | Green |
| 4,817,847 | A | 4/1989 | Redtenbacher et al. |
| 4,873,977 | A | 10/1989 | Avant et al. |
| 4,893,662 | A | 1/1990 | Gervasi |
| 4,903,697 | A | 2/1990 | Resnick et al. |
| 4,907,591 | A | 3/1990 | Vasconcellos et al. |
| 4,917,114 | A | 4/1990 | Green et al. |
| 4,957,499 | A | 9/1990 | Lipatov et al. |
| 4,962,877 | A | 10/1990 | Hervas |
| 5,005,749 | A | 4/1991 | Aranyi |
| 5,042,707 | A | 8/1991 | Taheri |
| 5,047,039 | A | 9/1991 | Avant et al. |
| 5,104,025 | A | 4/1992 | Main et al. |
| 5,119,983 | A | 6/1992 | Green et al. |
| 5,122,156 | A | 6/1992 | Granger et al. |
| 5,139,513 | A | 8/1992 | Segato |
| 5,158,222 | A | 10/1992 | Green et al. |
| 5,188,638 | A | 2/1993 | Tzakis |
| 5,193,731 | A | 3/1993 | Aranyi |
| 5,197,648 | A | 3/1993 | Gingold |
| 5,197,649 | A | 3/1993 | Bessler et al. |
| 5,205,459 | A | 4/1993 | Brinkerhoff et al. |
| 5,221,036 | A | 6/1993 | Takase |
| 5,222,963 | A | 6/1993 | Brinkerhoff et al. |
| 5,253,793 | A | 10/1993 | Green et al. |
| 5,261,920 | A | 11/1993 | Main et al. |
| 5,271,543 | A | 12/1993 | Grant et al. |
| 5,271,544 | A | 12/1993 | Fox et al. |
| 5,275,322 | A | 1/1994 | Brinkerhoff et al. |
| 5,282,810 | A | 2/1994 | Allen et al. |
| 5,285,944 | A | 2/1994 | Green et al. |
| 5,285,945 | A | 2/1994 | Brinkerhoff et al. |
| 5,292,053 | A | 3/1994 | Bilotti et al. |
| 5,309,927 | A | 5/1994 | Welch |
| 5,312,024 | A | 5/1994 | Grant et al. |
| 5,314,435 | A | 5/1994 | Green et al. |
| 5,314,436 | A | 5/1994 | Wilk |
| 5,330,486 | A | 7/1994 | Wilk |
| 5,333,773 | A | 8/1994 | Main et al. |
| 5,344,059 | A | 9/1994 | Green et al. |
| 5,346,115 | A | 9/1994 | Perouse et al. |
| 5,348,259 | A | 9/1994 | Blanco et al. |
| 5,350,104 | A | 9/1994 | Main et al. |
| 5,355,897 | A | 10/1994 | Pietrafitta et al. |
| 5,360,154 | A | 11/1994 | Green |
| 5,368,215 | A | 11/1994 | Green et al. |
| 5,392,979 | A | 2/1995 | Green et al. |
| 5,395,030 | A | 3/1995 | Kuramoto et al. |
| 5,403,333 | A | 4/1995 | Kaster et al. |
| 5,404,870 | A | 4/1995 | Brinkerhoff et al. |
| 5,411,508 | A | 5/1995 | Bessler et al. |
| 5,425,738 | A | 6/1995 | Gustafson et al. |
| 5,433,721 | A | 7/1995 | Hooven et al. |
| 5,437,684 | A | 8/1995 | Calabrese et al. |
| 5,439,156 | A | 8/1995 | Grant et al. |
| 5,443,198 | A | 8/1995 | Viola et al. |
| 5,447,514 | A | 9/1995 | Gerry et al. |
| 5,454,825 | A | 10/1995 | Van Leeuwen et al. |
| 5,464,144 | A | 11/1995 | Guy et al. |
| 5,464,415 | A | 11/1995 | Chen |
| 5,470,006 | A | 11/1995 | Rodak |
| 5,474,223 | A | 12/1995 | Viola et al. |
| 5,497,934 | A | 3/1996 | Brady et al. |
| 5,503,635 | A | 4/1996 | Sauer et al. |
| 5,522,534 | A | 6/1996 | Viola et al. |
| 5,533,661 | A | 7/1996 | Main et al. |
| 5,588,579 | A | 12/1996 | Schnut et al. |
| 5,609,285 | A | 3/1997 | Grant et al. |
| 5,626,591 | A | 5/1997 | Kockerling et al. |
| 5,632,433 | A | 5/1997 | Grant et al. |
| 5,639,008 | A | 6/1997 | Gallagher et al. |
| 5,641,111 | A | 6/1997 | Ahrens et al. |
| 5,658,300 | A | 8/1997 | Bito et al. |
| 5,669,918 | A | 9/1997 | Balazs et al. |
| 5,685,474 | A | 11/1997 | Seeber |
| 5,709,335 | A | 1/1998 | Heck |
| 5,715,987 | A | 2/1998 | Kelley et al. |
| 5,718,360 | A | 2/1998 | Green et al. |
| 5,720,755 | A | 2/1998 | Dakov |
| 5,732,872 | A | 3/1998 | Bolduc et al. |
| 5,749,896 | A | 5/1998 | Cook |
| 5,758,814 | A | 6/1998 | Gallagher et al. |
| 5,799,857 | A | 9/1998 | Robertson et al. |
| 5,814,055 | A | 9/1998 | Knodel et al. |
| 5,833,698 | A | 11/1998 | Hinchliffe et al. |
| 5,836,503 | A | 11/1998 | Ehrenfels et al. |
| 5,839,639 | A | 11/1998 | Sauer et al. |
| 5,855,312 | A | 1/1999 | Toledano |
| 5,860,581 | A | 1/1999 | Robertson et al. |
| 5,868,760 | A | 2/1999 | McGuckin, Jr. |
| 5,881,943 | A | 3/1999 | Heck et al. |
| 5,915,616 | A | 6/1999 | Viola et al. |
| 5,947,363 | A | 9/1999 | Bolduc et al. |
| 5,951,576 | A | 9/1999 | Wakabayashi |
| 5,957,363 | A | 9/1999 | Heck |
| 5,993,468 | A | 11/1999 | Rygaard |
| 6,024,748 | A | 2/2000 | Manzo et al. |
| 6,050,472 | A | 4/2000 | Shibata |
| 6,053,390 | A | 4/2000 | Green et al. |
| 6,068,636 | A | 5/2000 | Chen |
| 6,083,241 | A | 7/2000 | Longo et al. |
| 6,102,271 | A | 8/2000 | Longo et al. |
| 6,117,148 | A | 9/2000 | Ravo et al. |
| 6,119,913 | A | 9/2000 | Adams et al. |
| 6,126,058 | A | 10/2000 | Adams et al. |
| 6,142,933 | A | 11/2000 | Longo et al. |
| 6,149,667 | A | 11/2000 | Hovland et al. |
| 6,176,413 | B1 | 1/2001 | Heck et al. |
| 6,179,195 | B1 | 1/2001 | Adams et al. |
| 6,193,129 | B1 | 2/2001 | Bittner et al. |
| 6,203,553 | B1 | 3/2001 | Robertson et al. |
| 6,209,773 | B1 | 4/2001 | Bolduc et al. |
| 6,241,140 | B1 | 6/2001 | Adams et al. |
| 6,253,984 | B1 | 7/2001 | Heck et al. |
| 6,258,107 | B1 | 7/2001 | Balazs et al. |
| 6,264,086 | B1 | 7/2001 | McGuckin, Jr. |
| 6,269,997 | B1 | 8/2001 | Balazs et al. |
| 6,273,897 | B1 | 8/2001 | Dalessandro et al. |
| 6,279,809 | B1 | 8/2001 | Nicolo |
| 6,302,311 | B1 | 10/2001 | Adams et al. |
| 6,338,737 | B1 | 1/2002 | Toledano |
| 6,343,731 | B1 | 2/2002 | Adams et al. |
| 6,387,105 | B1 | 5/2002 | Gifford, III et al. |
| 6,398,795 | B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,136 B1 * | 9/2008 | Marczyk ........... A61B 17/07207 227/176.1 |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | | |
|---|---|---|---|
| 7,922,743 B2 | 4/2011 | Heinrich et al. | |
| 7,931,183 B2 | 4/2011 | Orban, III | |
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,012,170 B2 * | 9/2011 | Whitman | A61B 17/08 227/176.1 |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,405 B2 | 2/2012 | Milliman | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,801 B2 * | 10/2012 | Zemlok | A61B 90/90 227/176.1 |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,479,968 B2 | 7/2013 | Hodgkinson et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,627,994 B2 * | 1/2014 | Zemlok | A61B 90/90 227/176.1 |
| 8,627,995 B2 | 1/2014 | Smith et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,646,674 B2 | 2/2014 | Schulte et al. | |
| 8,662,370 B2 | 3/2014 | Takei | |
| 8,663,258 B2 | 3/2014 | Bettuchi et al. | |
| 8,672,207 B2 | 3/2014 | Shelton, IV et al. | |
| 8,672,931 B2 | 3/2014 | Goldboss et al. | |
| 8,672,951 B2 | 3/2014 | Smith et al. | |
| 8,678,264 B2 | 3/2014 | Racenet et al. | |
| 8,679,137 B2 | 3/2014 | Bauman et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,695,864 B1 | 4/2014 | Hausen | |
| 8,708,212 B2 | 4/2014 | Williams | |
| 8,733,611 B2 | 5/2014 | Milliman | |
| 8,733,615 B2 | 5/2014 | Nalagatla et al. | |
| 8,746,531 B2 | 6/2014 | Wenchell et al. | |
| 8,746,532 B2 | 6/2014 | Nalagatla et al. | |
| 8,783,543 B2 | 7/2014 | Shelton, IV et al. | |
| 8,789,737 B2 | 7/2014 | Hodgkinson et al. | |
| 8,800,838 B2 | 8/2014 | Shelton, IV | |
| 8,800,841 B2 | 8/2014 | Ellerhorst et al. | |
| 8,801,734 B2 | 8/2014 | Shelton, IV et al. | |
| 8,801,735 B2 | 8/2014 | Shelton, IV et al. | |
| 8,821,523 B2 | 9/2014 | Heinrich et al. | |
| 8,827,903 B2 | 9/2014 | Shelton, IV et al. | |
| 8,833,629 B2 | 9/2014 | Nalagatla et al. | |
| 8,840,004 B2 | 9/2014 | Holsten et al. | |
| 8,844,792 B2 | 9/2014 | Viola | |
| 8,845,661 B2 | 9/2014 | D'Arcangelo et al. | |
| 8,870,911 B2 | 10/2014 | Williams et al. | |
| 8,875,974 B2 | 11/2014 | Rebuffat et al. | |
| 8,893,948 B2 | 11/2014 | Williams | |
| 8,910,847 B2 | 12/2014 | Nalagatla et al. | |
| 8,925,785 B2 | 1/2015 | Holsten et al. | |
| 8,925,786 B2 | 1/2015 | Holsten et al. | |
| 8,967,448 B2 | 3/2015 | Carter et al. | |
| 8,978,955 B2 | 3/2015 | Aronhalt et al. | |
| 9,010,608 B2 | 4/2015 | Casasanta, Jr. et al. | |
| 9,010,612 B2 | 4/2015 | Stevenson et al. | |
| 9,016,540 B2 | 4/2015 | Whitman et al. | |
| 9,237,921 B2 * | 1/2016 | Messerly | A61B 17/320068 |
| 10,000,065 B1 * | 6/2018 | Baker | B41J 2/17503 |
| 10,201,365 B2 * | 2/2019 | Boudreaux | A61B 90/06 |
| 10,433,848 B2 | 10/2019 | Chen et al. | |
| 10,456,134 B2 | 10/2019 | DiNardo et al. | |
| 10,463,365 B2 | 11/2019 | Williams | |
| 10,463,373 B2 | 11/2019 | Mozdzierz et al. | |
| 10,463,374 B2 | 11/2019 | Sgroi, Jr. | |
| 10,470,770 B2 | 11/2019 | Shelton, IV et al. | |
| 10,470,771 B2 | 11/2019 | D'Agostino et al. | |
| 10,499,922 B2 | 12/2019 | Sgroi, Jr. | |
| 10,506,920 B2 | 12/2019 | Hasser et al. | |

(56) References Cited

U.S. PATENT DOCUMENTS

| | | | |
|---|---|---|---|
| 10,507,039 B2 | 12/2019 | Williams | |
| 10,512,467 B2 | 12/2019 | Swayze et al. | |
| 10,524,795 B2 | 1/2020 | Nalagatla et al. | |
| 10,524,798 B2 | 1/2020 | Williams | |
| 10,524,868 B2 | 1/2020 | Cooper et al. | |
| 10,537,331 B2 | 1/2020 | Scirica et al. | |
| 10,542,993 B2 | 1/2020 | Guerrera et al. | |
| 10,548,598 B2 | 2/2020 | Prescott et al. | |
| 10,561,424 B2 | 2/2020 | Penna et al. | |
| 10,568,631 B2 | 2/2020 | Rebuffat et al. | |
| 10,575,847 B2 | 3/2020 | Hessler et al. | |
| 10,595,871 B2 | 3/2020 | Racenet et al. | |
| 10,595,872 B2 | 3/2020 | Milliman | |
| 10,603,042 B2 | 3/2020 | Sgroi | |
| 10,624,646 B2 | 4/2020 | Bae et al. | |
| 10,639,041 B2 | 5/2020 | Williams | |
| 10,653,414 B2 | 5/2020 | Williams | |
| 11,045,199 B2* | 6/2021 | Mozdzierz | A61B 17/07207 |
| 11,596,400 B2* | 3/2023 | Mozdzierz | A61B 17/07207 |
| 2003/0111507 A1 | 6/2003 | Nunez | |
| 2004/0092992 A1* | 5/2004 | Adams | A61B 17/32002 606/180 |
| 2005/0051597 A1 | 3/2005 | Toledano | |
| 2005/0107813 A1 | 5/2005 | Gilete Garcia | |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2008/0245841 A1* | 10/2008 | Smith | A61B 17/07207 227/175.2 |
| 2008/0251568 A1* | 10/2008 | Zemlok | A61B 17/072 606/41 |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0069942 A1* | 3/2010 | Shelton, IV | A61B 17/07207 227/175.1 |
| 2010/0084453 A1 | 4/2010 | Hu | |
| 2010/0096431 A1* | 4/2010 | Smith | A61B 17/068 227/175.2 |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0270355 A1* | 10/2010 | Whitman | A61B 17/08 227/176.1 |
| 2010/0327041 A1 | 12/2010 | Milliman et al. | |
| 2011/0011916 A1 | 1/2011 | Levine | |
| 2011/0114697 A1 | 5/2011 | Baxter et al. | |
| 2011/0114700 A1 | 5/2011 | Baxter et al. | |
| 2011/0139851 A1* | 6/2011 | McCuen | A61B 17/07207 227/175.1 |
| 2011/0144640 A1 | 6/2011 | Heinrich et al. | |
| 2011/0155781 A1* | 6/2011 | Swensgard | A61B 17/068 227/176.1 |
| 2011/0192882 A1 | 8/2011 | Tess et al. | |
| 2011/0204119 A1* | 8/2011 | McCuen | A61B 17/07207 227/175.1 |
| 2011/0270355 A1* | 11/2011 | Chambers | H01R 24/58 607/57 |
| 2011/0288573 A1* | 11/2011 | Yates | A61B 34/30 227/175.1 |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0060258 A1 | 3/2013 | Giacomantonio | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153638 A1 | 6/2013 | Carter et al. | |
| 2013/0153639 A1 | 6/2013 | Hodgkinson et al. | |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181035 A1 | 7/2013 | Milliman | |
| 2013/0181036 A1 | 7/2013 | Olson et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193192 A1 | 8/2013 | Casasanta, Jr. et al. | |
| 2013/0200131 A1 | 8/2013 | Racenet et al. | |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |
| 2013/0248581 A1 | 9/2013 | Smith et al. | |
| 2013/0277411 A1 | 10/2013 | Hodgkinson et al. | |
| 2013/0277412 A1 | 10/2013 | Gresham et al. | |
| 2013/0284792 A1 | 10/2013 | Ma | |
| 2013/0292449 A1 | 11/2013 | Bettuchi et al. | |
| 2013/0299553 A1 | 11/2013 | Mozdzierz | |
| 2013/0299554 A1 | 11/2013 | Mozdzierz | |
| 2013/0306701 A1 | 11/2013 | Olson | |
| 2013/0306707 A1 | 11/2013 | Viola et al. | |
| 2014/0008413 A1 | 1/2014 | Williams | |
| 2014/0012317 A1 | 1/2014 | Orban et al. | |
| 2014/0046352 A1 | 2/2014 | Reboa et al. | |
| 2014/0158747 A1 | 6/2014 | Measamer et al. | |
| 2014/0246474 A1* | 9/2014 | Hall | A61B 34/74 227/175.1 |
| 2014/0284370 A1 | 9/2014 | Sahin | |
| 2015/0053749 A1* | 2/2015 | Shelton, IV | A61B 34/30 227/181.1 |
| 2015/0083772 A1 | 3/2015 | Miller et al. | |
| 2015/0173763 A1 | 6/2015 | Liu | |
| 2015/0209045 A1 | 7/2015 | Hodgkinson et al. | |
| 2016/0066916 A1* | 3/2016 | Overmyer | H02H 3/06 227/176.1 |
| 2016/0143641 A1 | 5/2016 | Sapienza et al. | |
| 2016/0157856 A1 | 6/2016 | Williams et al. | |
| 2016/0302792 A1 | 10/2016 | Motai | |
| 2017/0296185 A1* | 10/2017 | Swensgard | A61B 17/068 |
| 2017/0333033 A1* | 11/2017 | Valentine | A61B 17/068 |
| 2018/0353186 A1* | 12/2018 | Mozdzierz | A61B 17/072 |
| 2018/0360446 A1* | 12/2018 | Shelton, IV | A61B 17/068 |
| 2019/0099180 A1* | 4/2019 | Leimbach | A61B 17/07207 |
| 2019/0200998 A1 | 7/2019 | Shelton, IV et al. | |
| 2019/0201034 A1* | 7/2019 | Shelton, IV | A61B 18/00 |
| 2019/0314015 A1* | 10/2019 | Shelton, IV | A61B 17/07207 |
| 2020/0155149 A1* | 5/2020 | Calderoni | H01H 13/50 |
| 2020/0405304 A1* | 12/2020 | Mozdzierz | A61B 17/07207 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |

(56) References Cited

FOREIGN PATENT DOCUMENTS

| | | |
|---|---|---|
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3231373 A2 | 10/2017 |
| EP | 3417804 A1 | 12/2018 |
| EP | 3420972 A1 | 1/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2008107918 A1 | 9/2008 |

OTHER PUBLICATIONS

Extended European Search Report from Appl. No. 14181908.6 dated May 26, 2015.
European Examination Report from Appl. No.: 14181908.6 dated May 3, 2016.

* cited by examiner

CUT OPTIMIZATION FOR EXCESSIVE TISSUE CONDITIONS

CROSS-REFERENCE TO RELATED APPLICATIONS

This application claims the benefit of and priority to U.S. Provisional Patent Application Ser. No. 62/960,202 filed Jan. 13, 2020, the entire disclosure of which is incorporated by reference herein.

FIELD

The disclosure is directed to powered circular stapling devices and, more particularly, to optimizing the cutting stroke of powered circular stapling devices.

BACKGROUND

Conventional powered circular stapling devices typically include a one-time use circular reload releasably secured to a reusable adapter and/or a handle assembly. During a stapling procedure, two layers of tissue are clamped between the circular reload and an anvil assembly that is attached to a trocar of the adapter assembly. After the tissue is clamped between the circular reload and the anvil assembly to define a specific tissue gap between the circular reload and the anvil assembly, the handle assembly can be actuated to drive a staple pusher within the circular reload and advance staples through the tissue into staple pockets on the anvil assembly.

Subsequent to staple formation, the handle assembly can be actuated to drive a knife pusher within the circular reload at a steady speed to advance an annular knife from within the circular reload. As the annular knife is advanced, the annular knife engages and cuts a hole in the clamped and stapled tissue to form an anastomosis. The knife pusher is then retracted, returning the annular knife back into the circular reload to prevent exposure of the annular knife. The knife pusher may retract the annular knife beyond its initial position to, for example, engage detents which retain the annular knife within the circular reload.

Prior to advancing the knife pusher, a large amount of tissue may be captured within the circular reload and/or between the circular reload and the anvil assembly. Current software controls the annular knife by moving the knife pusher at a constant speed until a specified cut force limit, e.g., 275 lbf, is detected by a strain gage supported inside the handle assembly or adapter assembly. Excessive amounts of tissue inside the circular reload and/or between the circular reload and the anvil assembly during advancement of the knife assembly may raise the amount of pressure against the knife pusher assembly such that the cut force limit is reached prior to the annular knife completely cutting through the tissue. This may result in an incomplete cut.

Therefore, it would be beneficial to have a powered circular stapling device with an optimized cutting stroke for accommodating a large amount of tissue inside the circular reload.

SUMMARY

A method of operating a surgical stapler is provided. The method includes advancing a knife assembly at a first velocity until a predetermined force on the knife assembly is detected, advancing the knife assembly at a second velocity when the predetermined force is detected, the second velocity being less than the first velocity, and continuing to advance the knife assembly at the second velocity until the knife assembly travels a cutting stroke distance.

In embodiments, the first velocity is from about 3.5 in/min to about 4.0 in/min. The second velocity may be from about 0.25 in/min to about 0.5 in/min. The predetermined force may be about 275 lbf. The cutting stroke distance may be from about 0.20 in. to about 0.350 in. The cutting stroke distance may be about 0.325 in.

Another method of operating a surgical stapler is provided including advancing a knife assembly at a first velocity until a predetermined force on the knife assembly is detected, advancing the knife assembly at a second velocity when the predetermined force is detected, the second velocity being less than the first velocity, continuing to advance the knife assembly at the second velocity until a second predetermined force on the knife assembly is detected, and advancing the knife assembly at a third velocity until the knife assembly travels a cutting stroke distance.

In embodiments, the first velocity is from about 3.5 in/min to about 4.0 in/min. The second velocity may be from about 0.25 in/min to about 0.5 in/min. The predetermined force may be about 275 lbf. The cutting stroke distance may be from about 0.20 in. to about 0.350 in. The cutting stroke distance may be about 0.325 in.

BRIEF DESCRIPTION OF THE DRAWINGS

Various aspects of the disclosed circular reload are described herein below with reference to the drawings, wherein.

DETAILED DESCRIPTION

The disclosed circular reload will now be described in detail with reference to the drawings in which like reference numerals designate identical or corresponding elements in each of the several views. However, it is to be understood that the aspects of the disclosure provided herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Figure 1:
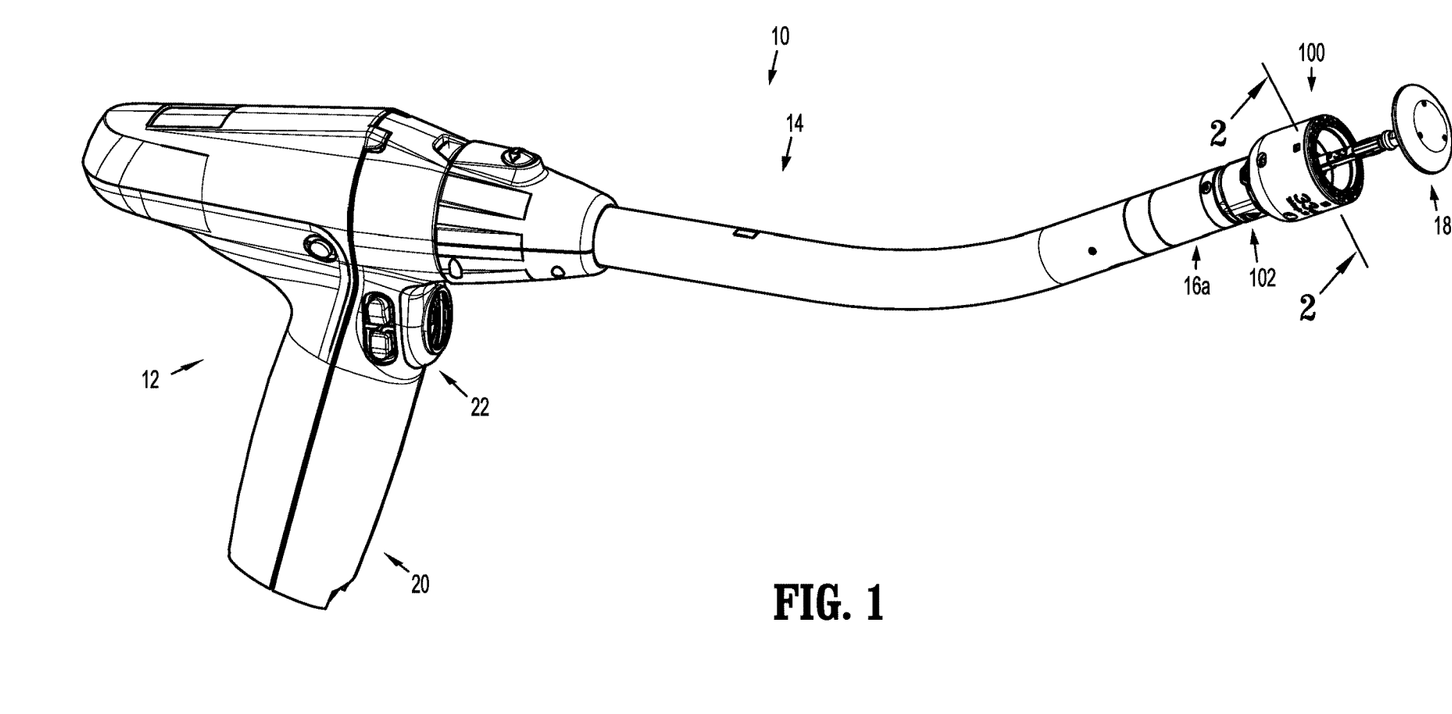
FIG. 1 is a side perspective view of a circular stapling device including exemplary aspects of the disclosed circular reload in accordance with the disclosure.
Figure 2:
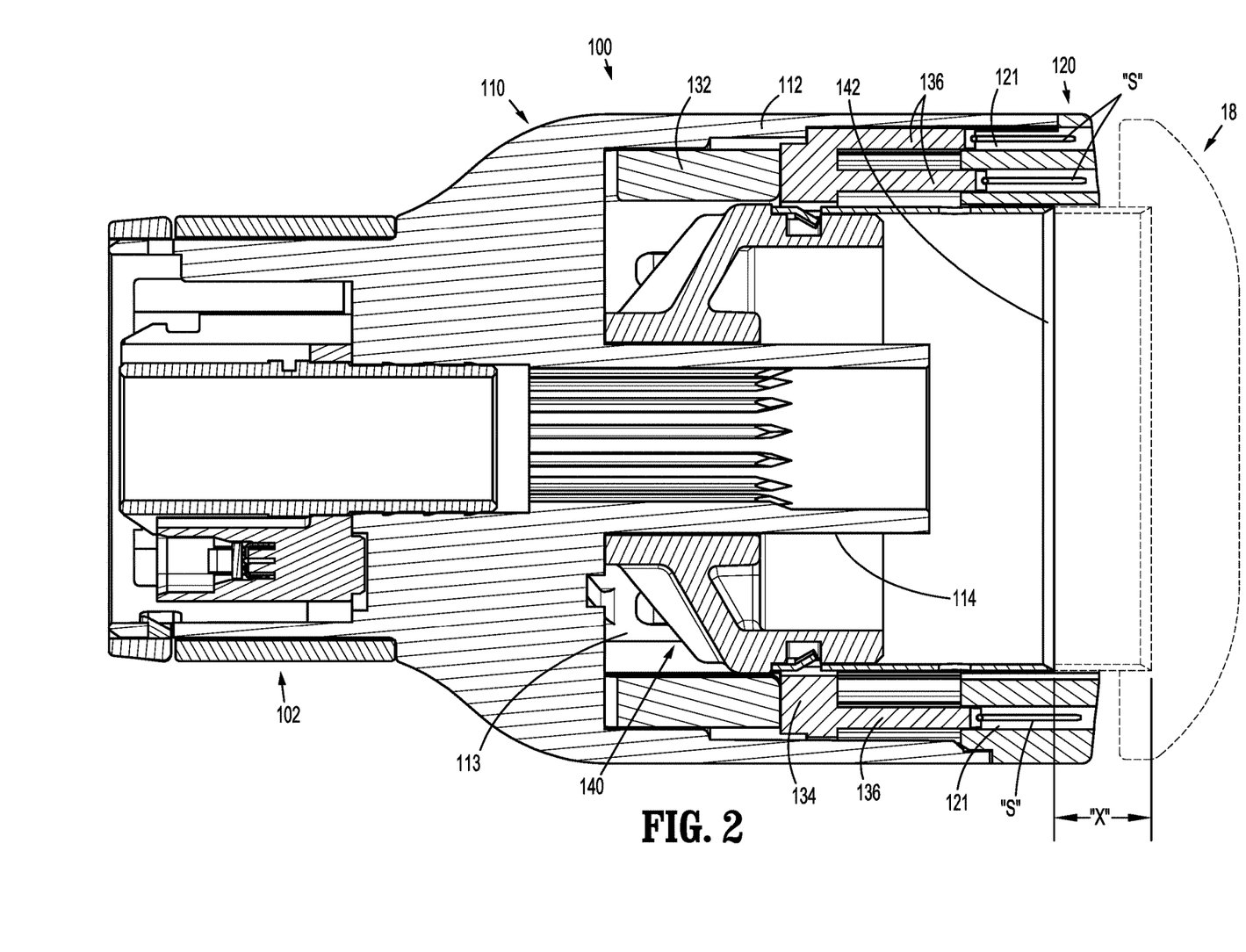
FIG. 2 is a side perspective view of the circular reload of FIG. 1.

FIGS. 1 and 2 illustrate a circular stapling device 10 including an exemplary circular reload shown generally as circular reload 100. The stapling device 10 includes a handle assembly 12, an elongate body or adaptor assembly 14, the circular reload 100, and an anvil assembly 18 that is supported for movement in relation to the circular reload 100 between spaced and approximated or clamped positions as is known in the art. The circular reload 100 includes a proximal portion 102 that is releasably coupled to a distal portion 16a of the elongate body 16. The handle assembly 12 includes a stationary grip 20 that supports actuation buttons 22 for controlling operation of various functions of the stapling device 10 including approximation of the circular reload 100 and anvil assembly 18, firing of staples from the circular reload 100, and cutting or coring of tissue (not shown) clamped between the circular reload 100 and the anvil assembly 18.

The stapling device 10 is illustrated as an electrically powered stapling device including an electrically powered handle assembly 12 that may support one or more batteries (not shown). The elongate body 14 is in the form of an adaptor assembly 14 that translates power from the handle assembly 12 to the circular reload 100 and anvil assembly 18. Examples of electrically powered stapling devices can be found in U.S. Pat. Nos. 9,055,943, 9,023,014, and U.S. Publication Nos. 2018/0125495 ("the '495 Publication"), and 2017/0340351.

FIG. 2 illustrates the circular reload 100 which includes a shell housing 110, a staple cartridge 120 supporting a plurality of staples "S", a staple pusher assembly 130, and a knife pusher assembly 140 that supports an annular knife 132. The staple cartridge 120 is annular and defines annular rows of staple pockets 121. Each of the staple pockets 121 supports one of the plurality of staples "S". The circular reload 100 will only be described in detail to the extent necessary to fully disclose the novel aspects of the disclosure. For a detailed description of an exemplary circular reload, please refer to the '495 Publication.

Briefly, the staple pusher assembly 130 of the circular reload 100 includes a staple pushing member 132 and an annular pusher 134. The annular pusher 134 of the circular reload 100 has a plurality of fingers 136. Each of the plurality of fingers 136 is received within a respective one of the staple pockets 121 of the staple cartridge 120 and is movable through the respective staple pocket 121 to eject the staples "S" from the staple pockets 121 when the staple pushing member 132 is moved from a retracted position to an advanced position within the shell housing 110.

The shell housing 110 of the circular reload 100 includes an outer housing portion 112 and an inner housing portion 114 spaced from the outer housing portion 112 to define an annular cavity 113. The pusher assembly 130 is movable within the annular cavity 113 between a retracted position (FIG. 2) and an advanced position (not shown) independently of the knife pusher assembly 140 to eject the staples "S" from the staple cartridge 120. The knife pusher assembly 140, including the annular knife 142, is movable from a retracted position (FIG. 2) to an advanced position (shown in phantom) to cut the tissue (not shown).

The distance between the position of the annular knife 142 when the knife pusher assembly 140 is in the retracted position and the position of the annular knife 142 when the knife pusher assembly 140 is in the advanced position is indicated in FIG. 2 as a cutting stroke distance "X". In embodiments, the cutting stroke distance "X" is from about 0.20 inches to about 0.35 inches. In certain embodiments, the cutting stroke distance "X" is about 0.325 inches. To ensure that the tissue (not shown) clamped between the circular reload 100 and the anvil assembly 18 is completely cut during a stapling procedure, it is necessary for the annular knife 142 to travel the entire cutting stroke distance "X".

To prevent damage to the components of the circular stapling device 10 during a stapling procedure, the force applied to knife pusher assembly 140 is typically limited to a predetermined force. For example, in certain aspects of the disclosure, the cut force limit is 275 lbf. However, during the stapling procedure, an excessive amount of tissue (not shown) may become trapped within the circular reload 100 and/or between the circular reload 100 and the anvil assembly 18 and may cause the cut force limit of the circular stapling device 10 to be reached before the annular knife 142 travels the entire cutting stroke distance "X". This may result in an incomplete cut of the tissue.

In order to compensate for excessive amounts of tissue that may be clamped between the circular reload 100 and the anvil assembly 18, software included with the circular stapling device 10 is programmed to reduce a speed of travel, i.e., velocity, of the knife pusher assembly 140, and more particularly, the annular knife 142, when the cut force limit is reached prior to the annular knife 142 travelling through the entire cutting stroke distance "X". The software may also increase the cut force limit. In aspects of the disclosure, the velocity of the annular knife 142 is reduced by 10%. In embodiments, a first or initial velocity of the knife pusher assembly 140 is from about 3.5 in/min to about 4.0 in/min. and a second velocity is from about 0.25 in/min to about 0.5 in/min. Simultaneously, the cut force limit may be increased to, for example, 350 lbf. By reducing the speed at which the annular knife 142 travels, the excess tissue trapped within the circular reload 100 and/or between the circular reload 100 and the anvil assembly 18 is able to relax, i.e., release fluid, and return to a state of equilibrium.

In instances where the initial velocity of the annular knife 142 is reduced to the second velocity and the increased cut force limit is attained before the annular knife 142 travels the entire cutting stroke distance "X", the velocity of the annular knife 142 may be further reduced to a third velocity. The further reduction in velocity may also be accompanied by an increase in the cut force limit. Subsequent reductions in velocity of the annular knife 142 and increases in the cut force limit may occur until the annular knife 142 travels the entire cutting stroke distance "X".

Figure 3:
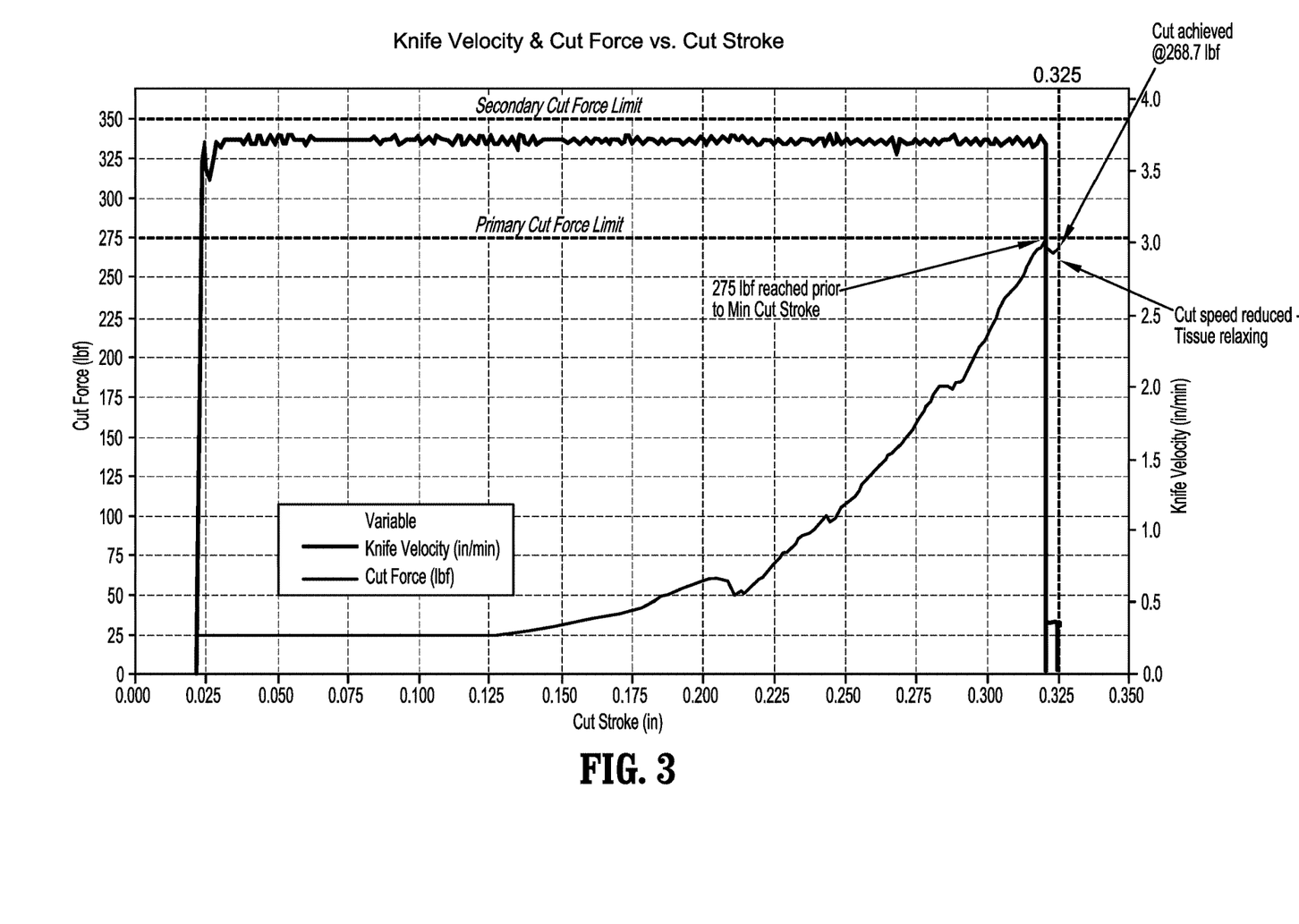
FIG. 3 is a chart plotting knife velocity and cut force relative to cut stroke.

As illustrated in the chart of FIG. 3, by reducing the speed of the annular knife 142 to allow time for the tissue clamped within the circular reload 100 to relax, the cut force required to move the annular knife 142 through the entire cut stroke distance "X" is reduced.

In other aspects of the disclosure, the annular knife 142 may be moved at an initial velocity until the annular knife 142 experiences resistance, i.e., the annular knife 142 engages tissue. The velocity of the annular knife 142 may then be reduced, as described above, until the annular knife 142 travels the entire cutting stroke distance "X". Increasing the velocity of the annular knife 142 prior to the annular knife 142 engaging tissue reduces firing time of the surgical stapling device 10 when the annular knife 142 travels through the circular reload 100.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A method of operating a surgical stapler, the method comprising:
    advancing an annular knife of a knife assembly at a first velocity until a predetermined force on the knife assembly is detected;
    increasing force applied by the annular knife above the predetermined force in response to the annular knife reaching a first position;
    determining that the annular knife reached a second position distal of the first position, the distance travelled in reaching the second position corresponding to a minimum cutting stroke;
    after the minimum cutting stroke is achieved advancing the annular knife at a second velocity when the force above the predetermined force is detected, the second velocity being less than the first velocity; and
    continuing to advance the annular knife at the second velocity until the annular knife travels a cutting stroke distance.

2. The method of claim 1, wherein the first velocity is from about 3.5 in/min to about 4.0 in/min.

3. The method of claim 1, wherein the second velocity is from about 0.25 in/min to about 0.5 in/min.

4. The method of claim 1, wherein the predetermined force is about 275 lbf.

5. The method of claim 1, wherein the cutting stroke distance is from about 0.20 in. to about 0.350 in.

6. The method of claim 5, wherein the cutting stroke distance is about 0.325 in.

7. The method of claim 1, wherein the predetermined force occurs when the knife assembly engages tissue.

8. A method of operating a surgical stapler, the method comprising:
    advancing an annular knife of a knife assembly at a first velocity until a first predetermined force on the knife assembly is detected;
    determining that a minimum cutting stroke distance is achieved;
    after the minimum cutting stroke is achieved advancing the annular knife at a second velocity when the first predetermined force is detected, the second velocity being less than the first velocity;
    continuing to advance the annular knife at the second velocity until a second predetermined force on the knife assembly is detected; and
    advancing the annular knife at a third velocity until the annular knife travels a cutting stroke distance.

9. The method of claim 8, wherein the first velocity is from about 3.5 in/min to about 4.0 in/min.

10. The method of claim 8, wherein the second velocity is from about 0.25 in/min to about 0.5 in/min.

11. The method of claim 8, wherein the first predetermined force is about 275 lbf.

12. The method of claim 8, wherein the cutting stroke distance is from about 0.20 in. to about 0.350 in.

13. The method of claim 12, wherein the cutting stroke distance is about 0.325 in.

14. The method of claim 8, wherein the first predetermined force occurs when the knife assembly engages tissue.

15. A method of operating a surgical stapler, the method comprising:
    advancing a staple pusher through a stapling stroke to staple tissue until a predetermined force on the staple pusher is detected;
    increasing force applied by the staple pusher above the predetermined force in response to the staple pusher reaching a first position;
    determining that a minimum cutting stroke distance is achieved, wherein the minimum cutting stroke distance corresponds to a distance travelled in reaching a second position distal of the first position;
    after the minimum cutting stroke is achieved advancing a knife assembly at a first velocity until a knife of the knife assembly engages the stapled tissue;
    advancing the knife assembly at a second velocity when the knife assembly engages the stapled tissue, the second velocity being less than the first velocity; and
    continuing to advance the knife assembly at the second velocity until the knife travels a cutting stroke distance through the stapled tissue.

16. The method of claim 15, wherein advancing the knife assembly at a first velocity until the knife of the knife assembly engages the stapled tissue includes advancing an annular knife.

17. The method of claim 15, wherein the first velocity is from about 3.5 in/min to about 4.0 in/min.

18. The method of claim 15, wherein the second velocity is from about 0.25 in/min to about 0.5 in/min.

19. The method of claim 15, wherein the cutting stroke distance is from about 0.20 in. to about 0.350 in.

20. The method of claim 15, wherein the cutting stroke distance is about 0.325 in.

* * * * *